US008864661B2

(12) United States Patent
Olsen (10) Patent No.: US 8,864,661 B2
(45) Date of Patent: Oct. 21, 2014

(54) TRANSORAL RETRACTOR FOR ROBOTIC SURGERY (75) Inventor: Steven M. Olsen, Hood River, OR (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 13/981,019

(22) PCT Filed: Jan. 25, 2012

(86) PCT No.: PCT/US2012/022497
§ 371 (c)(1),
(2), (4) Date: Jul. 22, 2013

(87) PCT Pub. No.: WO2012/103180
PCT Pub. Date: Aug. 2, 2012

(65) Prior Publication Data
US 2013/0296654 A1 Nov. 7, 2013

Related U.S. Application Data (60) Provisional application No. 61/436,729, filed on Jan. 27, 2011.

(51) Int. Cl.
A61B 1/32 (2006.01)
A61B 17/02 (2006.01)
A61B 1/00 (2006.01)
A61B 1/24 (2006.01)

(52) U.S. Cl.
CPC ...... A61B 1/24 (2013.01); A61B 1/32 (2013.01); A61B 17/0293 (2013.01); A61B 1/00094 (2013.01)
USPC ............ 600/237; 600/210; 600/231; 600/239

(58) Field of Classification Search
USPC .................................. 600/184–246
See application file for complete search history.

(56) References Cited

U.S. PATENT DOCUMENTS

| 5,178,132 | A | * | 1/1993 | Mahefky .................. 600/194 |
| 5,897,491 | A | | 4/1999 | Kastenbauer et al. |
| 5,971,920 | A | | 10/1999 | Nagel |
| 6,322,501 | B1 | | 11/2001 | Fernot |
| RE37,861 | E | | 9/2002 | Schneider |
| D510,768 | S | | 10/2005 | Farley |

(Continued)

OTHER PUBLICATIONS

Young Min Park, MD et al. "Transoral robotic surgery (TORS) in laryngeal and hypopharyngeal cancer", Journal of Laparoendoscopic & Advanced Surgical Techniques, vol. 19, No. 3, 2009, 2 pages.

(Continued)

Primary Examiner — Pedro Philogene
Assistant Examiner — Christina Negrellirodrigue
(74) Attorney, Agent, or Firm — Faegre Baker Daniels LLP (57) ABSTRACT A transoral retractor in accordance with one embodiment of the invention includes a handle, a retractor blade mount attached to the handle, a frame and a pivot mechanism to pivotally mount the frame to the handle. In another embodiment the frame includes side members and is configured with the side members at transverse locations that will be near or beyond the side of the patient's head. The frame and/or pivot mechanism are configured to locate a plane of the frame generally at or near the plane of the patient's oral commissaries, with the side members located below the plane of the oral commissaries.

7 Claims, 14 Drawing Sheets

(56) References Cited

U.S. PATENT DOCUMENTS

| | | | |
|---|---|---|---|
| 7,887,483 B2 * | 2/2011 | Rosenberg | 600/238 |
| 2007/0287889 A1 | 12/2007 | Mohr | |
| 2008/0033249 A1 | 2/2008 | Sakamoto | |
| 2008/0319270 A1 * | 12/2008 | Rosenberg | 600/238 |
| 2011/0060192 A1 * | 3/2011 | Pastron | 600/205 |

OTHER PUBLICATIONS

Explorent, FK Laryngo-Pharyngoscope, Jan. 2003, 40 pages.

Bert W. O'Malley, Jr. et al., "Transoral robotic surgery (TORS) for base of tongue neoplasms", The Laryngoscope, 116, Aug. 2006, 8 pages.

daVinci Transoral Surgery Procedure Guide, Aug. 2008, 31 pages.

* cited by examiner

TRANSORAL RETRACTOR FOR ROBOTIC SURGERY

TECHNICAL FIELD

The invention relates generally to surgical retractors. In particular, the invention is a transoral retractor for use in conjunction with robotic surgical systems.

BACKGROUND OF THE INVENTION

Transoral retractors, devices used to provide access to a patient's oral cavity and larynopharynx during surgical procedures performed through the oral cavity, are generally known. By way of example, one such known device, the FK retractor, is distributed by Gyrus Medical GmbH and disclosed in the Kastenbauer U.S. Pat. No. 5,897,491.

There remains, however, a continuing need for improved transoral retractors. In particular, there is a need for transoral retractors for us in connection with robotic surgical systems.

SUMMARY OF THE INVENTION

One embodiment of the invention is a transoral retractor designed to provide exposure of the oral cavity, pharynx, larynx, and upper esophagus for robotic head and neck surgery. The retractor includes a universal handle which articulates with either a gallows or standard laryngoscope chest brace. The handle interfaces with interchangeable spatula blades whose proximal end attaches to the handle at variable lengths depending on patient size and target tissue. The midbody of the spatula blade is designed to elevate and retract the body of the tongue away from the surgical field, and the distal end is designed to interface with and expose the target area of the upper aerodigestive tract. The spatula blades are designed to distribute pressure evenly on the surface of the tongue and to prevent the tongue from prolapsing into the surgical field. The spatula blades may be curved upward along the vertical axis decreasing the pressure needed expose the distal laryngopharynx. Each blade is fitted with a tubular element with a universal suction adapter on the proximal end allowing for smoke evacuation during surgery. The handle articulates with a telescoping frame designed to provide wide oral opening. The frame is designed to sit below the plane of the oral commisures. Along the frame attach a variety of retraction devices. Furthermore, the frame pivots and locks along a horizontal plane perpendicular to the long axis of the spatula blades allowing the retractor blade to be inserted at any of a wide range of angles relative to the frame. The device can be equipped with spatula blades designed to interface with the lower teeth widely opening the mouth. Sutures can then be used to retract the tongue or other aerodigestive tract tissues and can be fixed to rotation and locking pins or knobs located on the frame and handle to provide precise tissue retraction. The device provides a wide aperture through the oral cavity for introduction of robotic and handheld surgical devices while protecting the patient's normal tissue and optimally exposing the target tissues.

DETAILED DESCRIPTION

A transoral retractor 10 in accordance with one embodiment of the present invention can be described with reference to FIGS. 1-7. As described in greater detail below, retractor 10 is particularly well suited for use in connection with aerodigestive tract robotic surgery, although the device can also be used in other applications such as surgical procedures with conventional handheld instruments. As shown, the retractor 10 includes an attachment handle 12 and a face frame 14 pivotally mounted to the handle. The handle 12 includes an attachment structure 16 for mounting the retractor 10 to a support structure such as a conventional laryngoscope chest brace or gallows suspension (not shown). In the embodiment shown in FIG. 2 the attachment structure 16 is universal adapter that includes an elongated bore for receiving an end of a support structure mounting arm 18, and a threaded knob 20 for releasably securing the mounting arm in the bore. A spatula blade 22 is shown attached to the end of the handle 12 in FIGS. 2 and 3. The attachment structure 16 enables a gallows suspension (not shown) to be rotated to allow the angle of the spatula blade 22 or other retractor blades mounted to the retractor 10 to provide optimal exposure. Similarly, the illustrated attachment structure allows the retractor handle 12 to articulate with a conventional laryngoscope chest brace (not shown) to provide suspension and rotation of the retractor blade 22.

The handle 12 includes a base member 24 and an attachment mount 26 at one end. In the illustrated embodiment the attachment mount 26 is a universal-type mount configured to interchangeably receive the mount structure on the proximal ends of retractor accessories such as the spatula blade 22. The attachment mount 26 also enables the length of the spatula blade 22 extending from the handle into the patient to be adjusted to variable lengths depending on factors such as patient size and target tissue. A threaded knob 28 on the attachment mount 26 can be used to releasable secure the spatula blade 22 or other accessories to the handle 12. The attachment mount 26 is mounted to the base member 24 by an extension adjustment mechanism including knob 30, guide 32, extension shaft 33 and slot 34. By actuating the knob 30, the position of the attachment mount 26 and spatula blade 22 can be adjusted. In the illustrated embodiment the extension adjustment mechanism telescopes and positions the attachment mount 26 along a longitudinal axis with respect to the base member 24. In other embodiments (not shown) the extension adjustment mechanism can move and position the attachment mount about other degrees of motion.

Face frame 14 provides a wide oral opening by telescoping from the handle 12 to distract the upper and lower jaw. It also provides a fixation point for suture retraction, lateral oral commisure guards, lip protection, endotracheal tube retraction and control, and adjustable malleable retractors. As shown, frame 14 is pivotally mounted to the handle 12 by a pivot mechanism 40 and includes proximal mounting members 42, a distal transverse member 44 and side members 46. The pivot mechanism 40 includes a bracket 50 mounted to the handle 12 and rotating brackets 52 on the opposite sides of the bracket 50. As shown, the mounting members 42 of the frame 14 are mounted to the rotating brackets 52. The rotating brackets 52 enable the frame 14 to articulate with respect to the handle 12 about an axis extending transverse to the handle and through the brackets. The rotational position of the frame 14 with respect to the handle 12 can be releasably secured by the threaded knobs 54. In the illustrated embodiment pins 55 extend from the bracket 50. The pins 55 can be mounted to threaded bores (not visible) in the bracket 50. Pins 55 can be used as fixation points to secure (e.g., tie or wrap) sutures used on the patient during surgery. Other embodiments of the invention (not shown) have other structures such as clips, springs or cleats for suture fixation structures. In yet other embodiments (not shown) suture fixation structures such as pins 55 are mounted to other locations on the handle 12 and/or frame 14 for use during surgical procedures.

Figure 5:
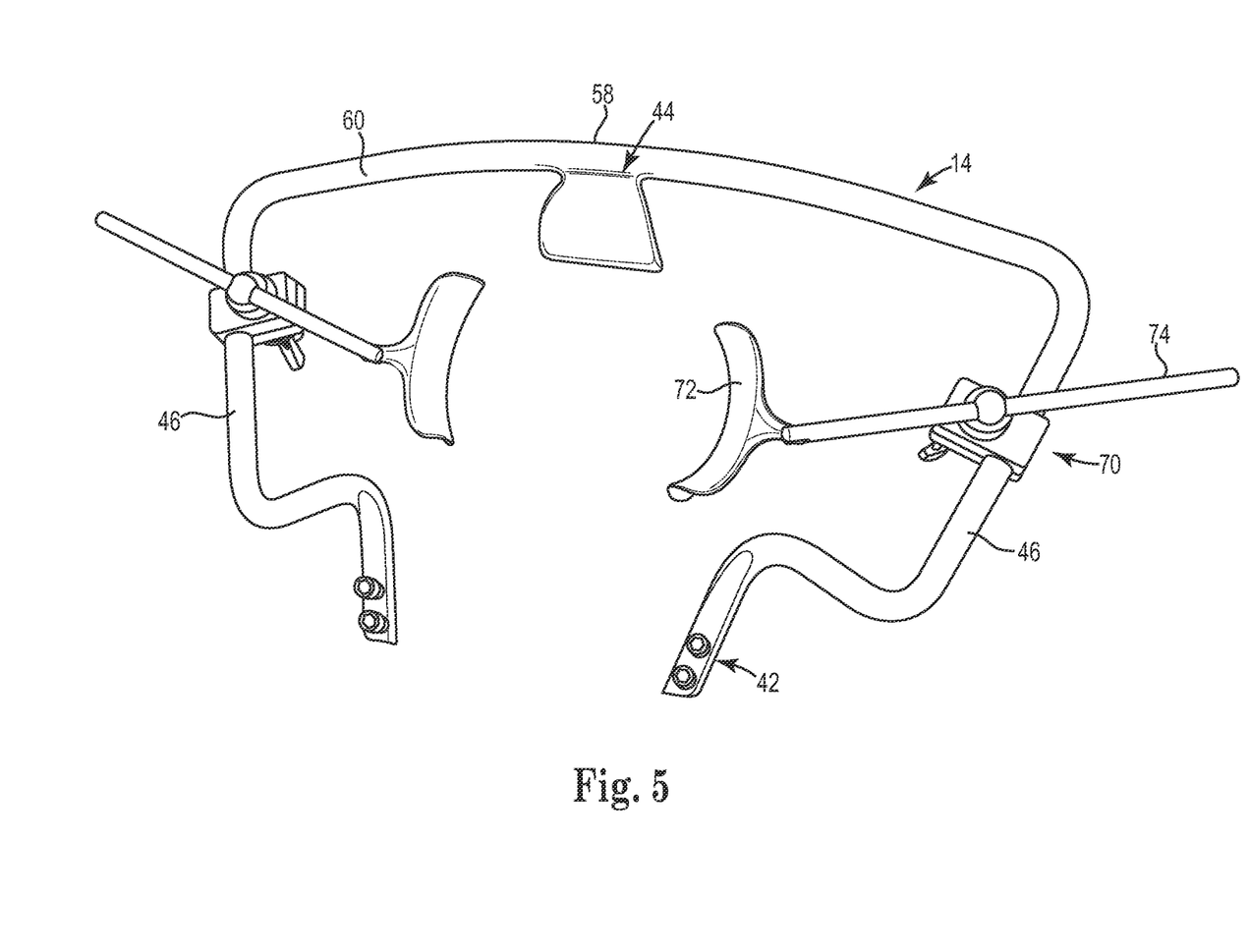
FIG. 5 is an isometric top (patient-facing) view of the frame of the transoral retractor shown in FIG. 1.
Figure 6:
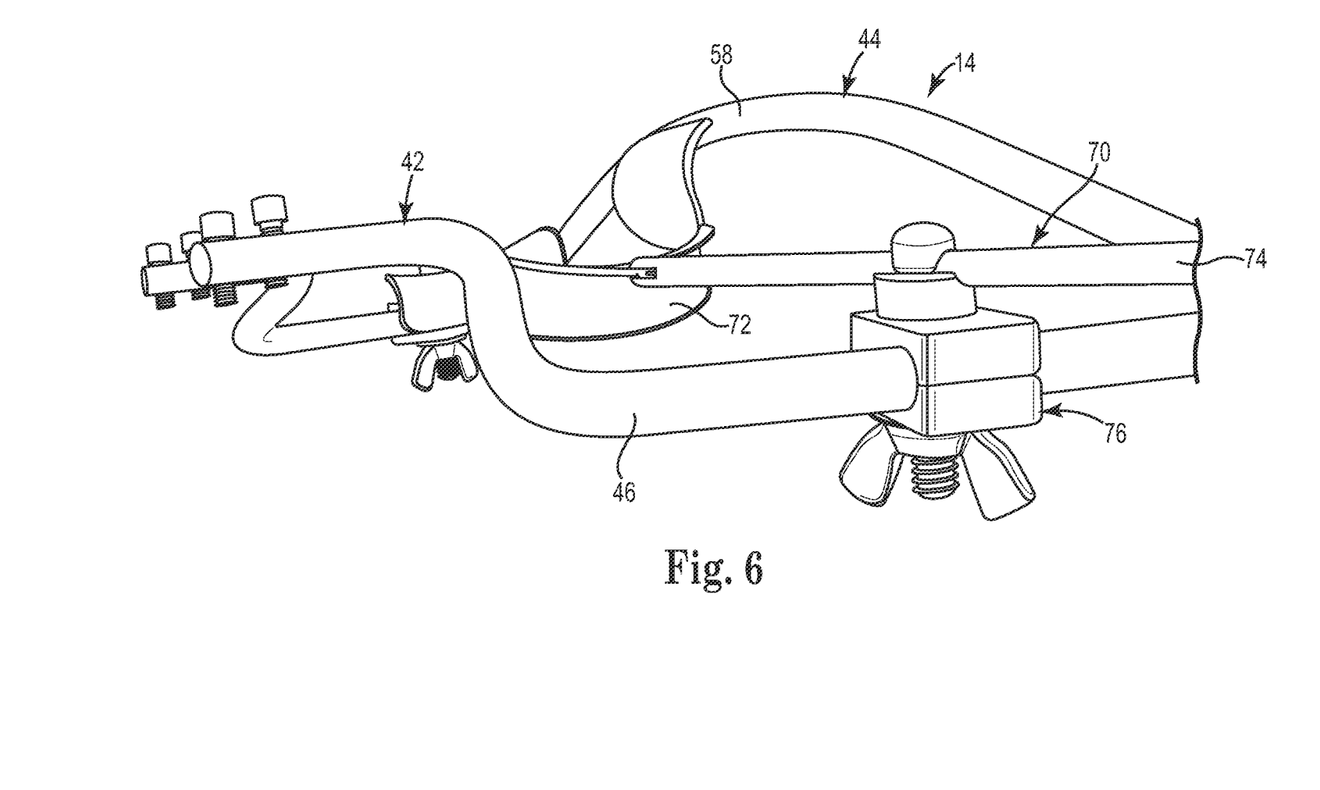
FIG. 6 is an isometric side view of the frame of the transoral retractor shown in FIG. 1.
Figure 7:
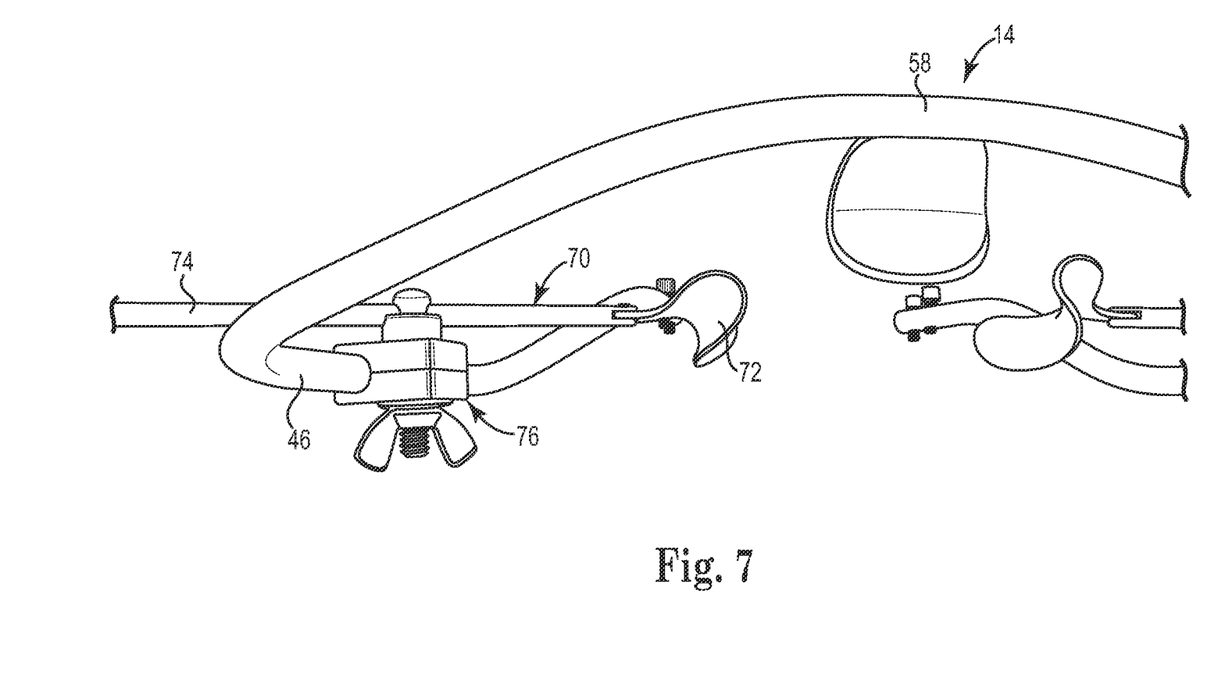
FIG. 7 is an isometric distal end view of the frame of the transoral retractor shown in FIG. 1.
Figure 8:
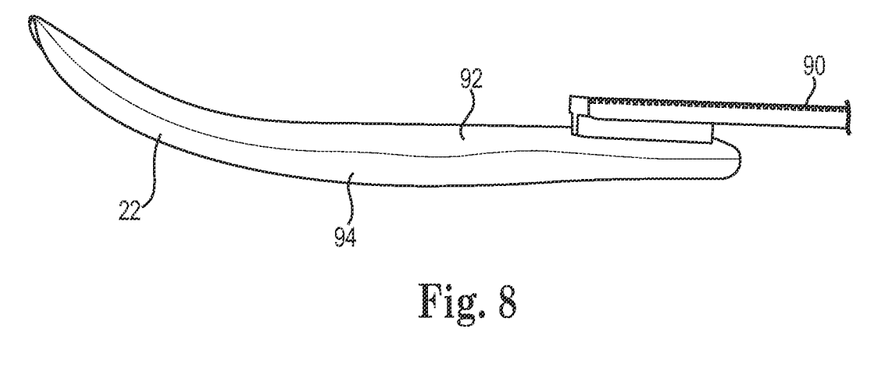
FIG. 8 is an isometric side view of the spatula blade shown in FIG. 1.
Figure 9:
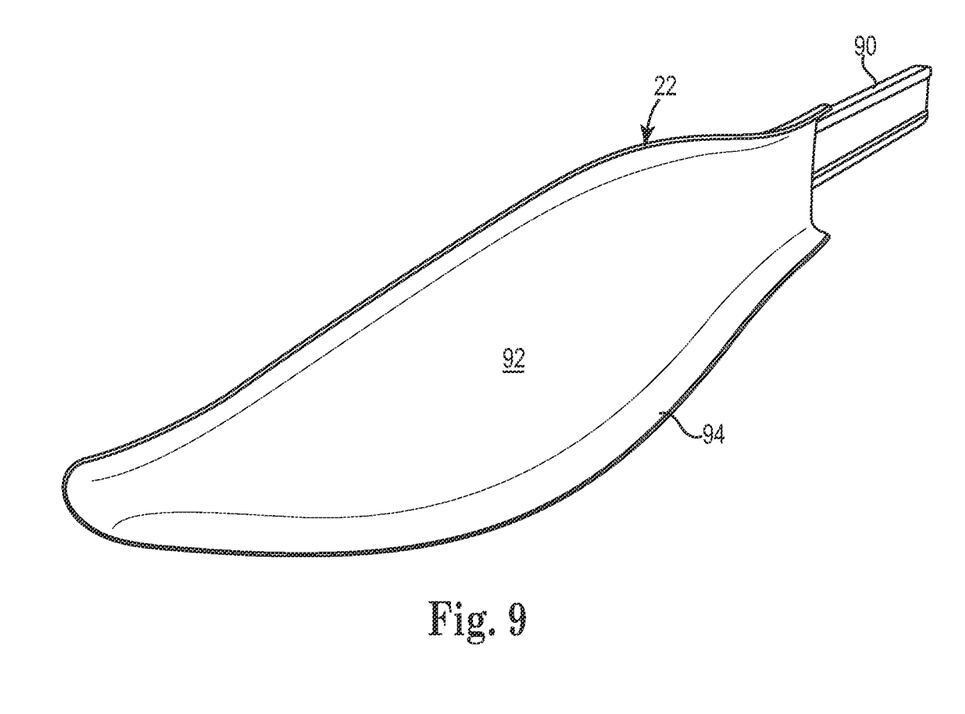
FIG. 9 is an isometric bottom view of the spatula blade shown in FIG. 1.
Figure 10:
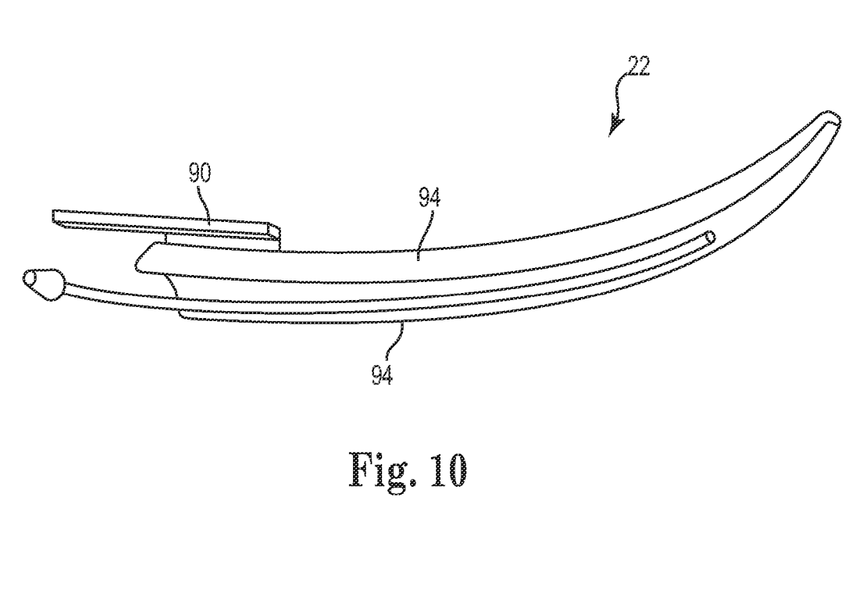
FIG. 10 is an isometric side view of the spatula blade shown in FIG. 1, showing the bottom of the blade and the suction tube.
Figure 11:
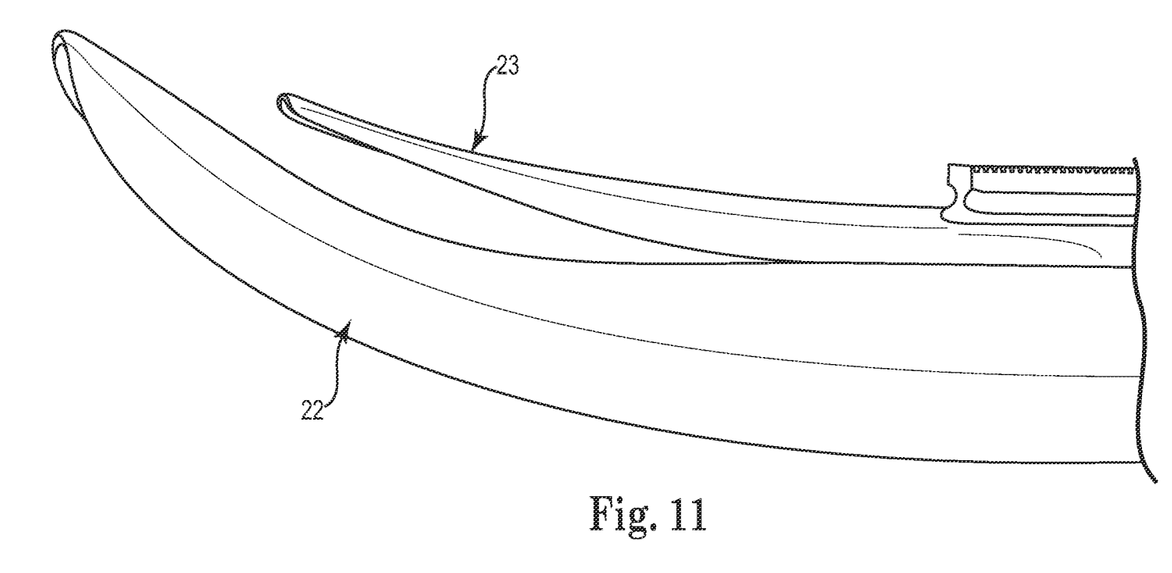
FIG. 11 is an isometric side view of the spatula blade shown in FIG. 1 and a second spatula blade in accordance with another embodiment of the invention.
Figure 12:
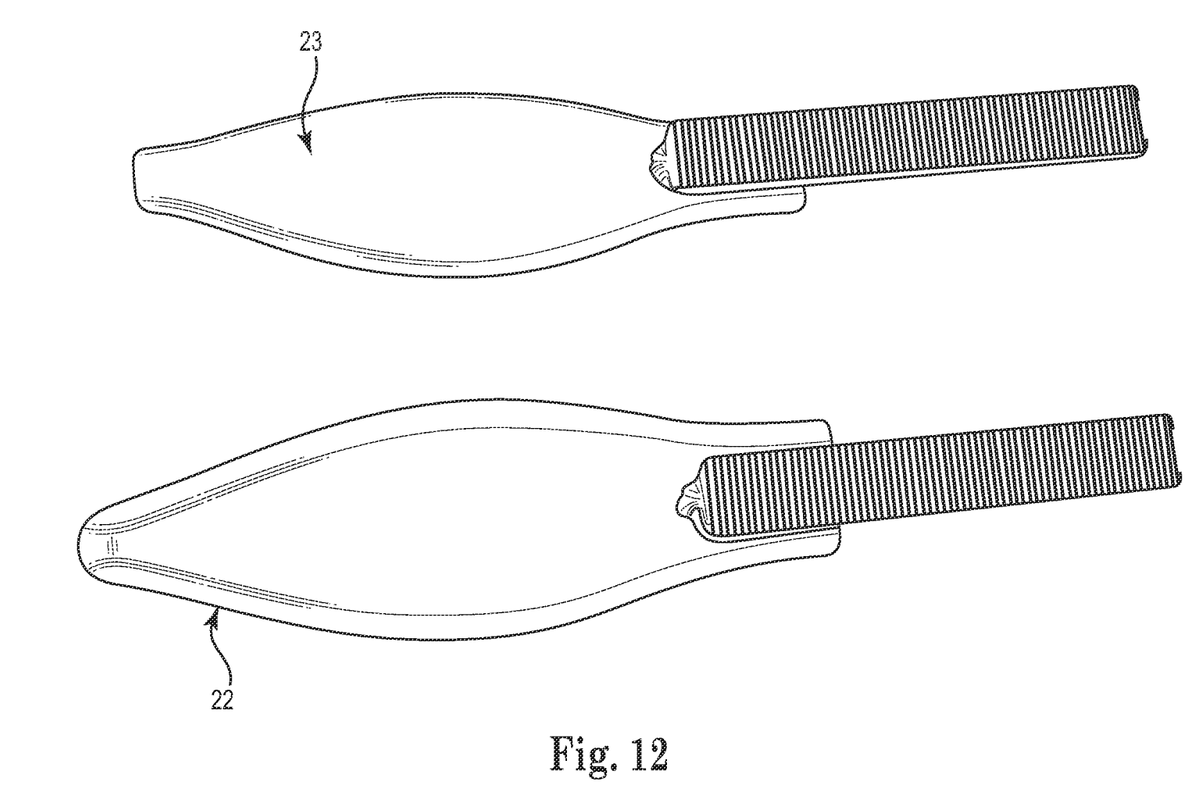
FIG. 12 is a top view of the spatula blades shown in FIG. 11.
Figure 13:
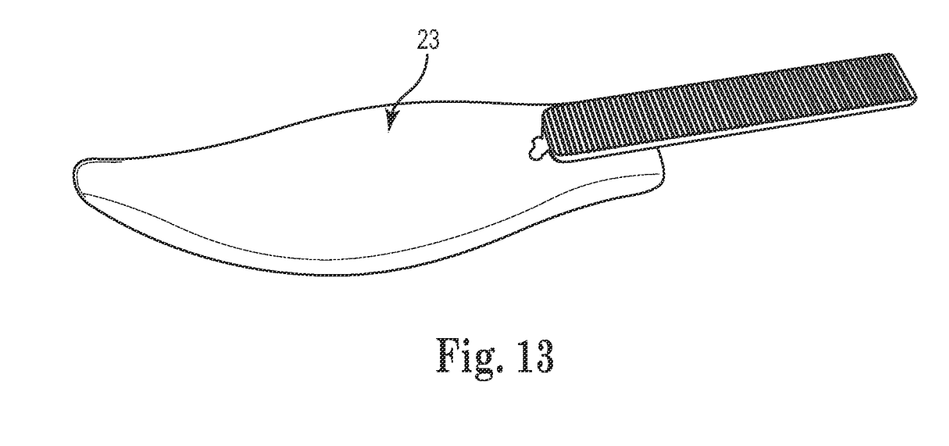
FIG. 13 is an isometric view of the second spatula blade shown in FIG. 11.
Figure 14:
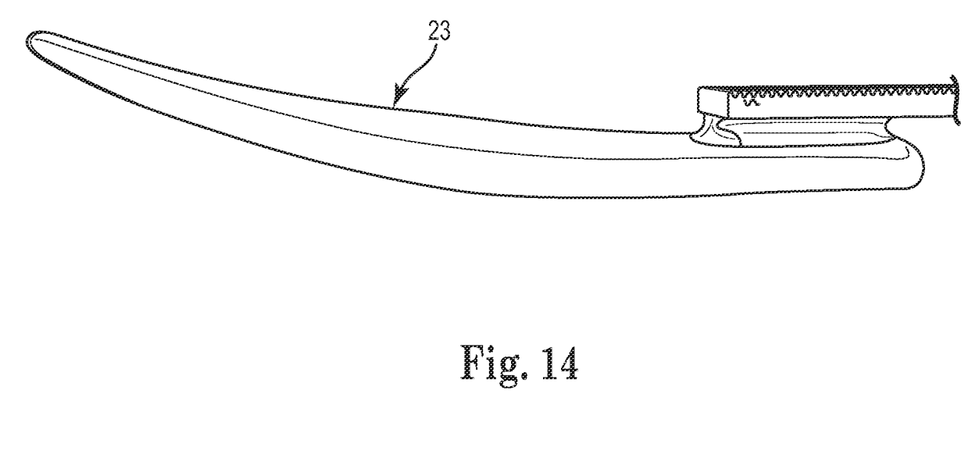
FIG. 14 is an isometric side view of the spatula blade shown in FIG. 13.

Distal transverse member 44 has a central portion 58 and a pair of end portions 60 that extend from opposite ends of the central portion. The proximal mounting members 42 include end portions 43 that connect to the pivot mechanism 40 and transversely extending portions 45 that extend between the end portions and the frame side members 46. The side members 46 of the frame 14 extend between the ends of the transverse member 44 and the ends of the mounting members 42 opposite the pivot mechanism 40. The mounting members 42 and distal transverse member 44 are configured with a sufficient length or other structural features to locate the side members 46 near or transversely beyond the sides of the patient's head during use. The frame 14 and/or pivot mechanism 40 are also configured to locate at least portions of the plane of the frame 14 in or below the plane of the patient's oral commisures. In the illustrated embodiment, for example, the distal transverse member 44 is arcuate in shape and the end portions 60 of the transverse member curve or extend at an angle in the patient-facing direction from the central portion 58. The transversely extending portions 45 of the proximal mounting members 42 similarly extend at an angle in the patient-facing direction from the end portions 43. The frame side members 46 are thereby located in a plane closer to the patient than a plane defined by the central portion 58 and or/the pivot mechanism 40. In one embodiment of the invention, the frame 14 is configured in such a manner that when the side members 46 are resting on a planar surface, the central portion 58 of the frame is a greater distance from the resting plane than the ends of the end portions 43 of the mounting members 42. The frame 14 pivots and locks along a horizontal plane perpendicular to the longitudinal axis of the spatula blade 22, allowing the blade to be inserted at a wide range of angles with respect to the frame.

By way of example, in one embodiment of the invention the ends of the frame side members 46 that intersect the transversely extending portions 45 are transversely spaced by about 181 mm. The ends of the transversely extending portions 45 that intersect the end portions 43 are transversely spaced by about 110 mm. The ends of the frame side members 46 that intersect the ends of the transverse member 44 are transversely spaced by about 245 mm. The ends of the frame side members 46 that intersect the transversely extending portions 45 are spaced from the transverse member 44 in a direction parallel to the handle 12 by about 100 mm. The ends of the transversely extending portions 45 that intersect the end portions 43 are spaced from the transverse member 44 in a direction parallel to the handle 12 by about 90 mm. The transverse distance between the ends of the end portions 43 that are mounted to the pivot mechanism 40 are transversely spaced from one another by about 78 mm. The distance in height between the frame side members 46 and the central portion 58 of the frame transverse member 44 is about 4.4 cm. Other embodiments of the invention have different dimensional features.

Lateral oral commisure guards 70 can be mounted to the side members 46 of the frame 14, or at other locations on the frame such as mounting members 42 or distal transverse member 44. In the illustrated embodiment of the invention the lateral guards 70 include retractor blades 72 extending from arms 74, and adjustable mounts 76 for adjustably securing the blades and arms to the frame at positions and orientations selected by the surgeon. The retractor blades 72 can be formed from malleable metal, enabling a surgeon to bend and shape the blades in a personalized manner as appropriate for an individual patient. An upper jaw retractor blade 80 extends from the central portion 58 of the frame in a patient facing direction. In one embodiment the frame side members 46 are oriented lower than the oral commisure guards 70. This configuration can, for example, be achieved by pivoting the adjustable mounts 76 such that arms 74 are located above the side members 46, substantially parallel to the plane defined by frame 14 and extending in a patient facing direction. Other approaches for achieving this configuration can also be used.

A spatula blade 22 in accordance with one embodiment of the invention can be described with reference to FIGS. 8-12. As shown, the blade 22 includes a proximal mounting portion 90 for engagement with the attachment mount 26 on the handle 12, a major surface 92 and flanges 94 on its opposite sides. The midbody width of a spatula blade 22 designed to retain the patient's tongue will typically range from about 2.7-4.2 cm and is optimally sized to fit between the interdental arch of the mandible (which typically varies from about 3-4.5 cm in size) and to distribute forces evenly along the tongue to prevent the tongue from prolapsing into the cavity. The lateral flanges 94 on the midbody of the blade 22 may be flared up or down to either maximally trap the tongue, or to rest flush along the inner aspect of the mandible depending on the target tissue of interest. Distally, the blade width and shape is customized to the target tissue i.e. tonsil, base of tongue, supraglottis, glottis, etc. The blade 22 may utilize a curve along the long vertical access to reduce the amount of pressure needed to distribute force along the tongue. In one embodiment, for example, the curve of the blade 22 causes the surface 92 of the blade to change between about 0 degrees and 30 degrees over its length, with a 0-4 cm rise in height of the blade tip above the plane defined by the proximal portion of the blade. In other embodiments the tip of the blade 22 extends upward by a vertical distance that is greater or lesser than 4 cm. For example, in some embodiments the tip of the blade 22 extends upwardly by a vertical distance between 1-4 cms. Blade 22 has a generally continuously curved section extending from the tip or distal end toward the proximal end. Blade 22 is fitted with a tubular suction port 96 which terminates near the lateral tip of the blade to allow for smoke evacuation. For oral cavity and tongue base surgery, a short blade 22 could be used to articulate with the mandibular teeth only and tongue and other soft tissue retraction could be performed with sutures placed through the tissue and secured to pins 55 on the handle 12 or frame 14. Alternative separate blades include but are not limited to a mandibular tooth blade, central and right and left tongue base blades, left and right tonsil blades, central supraglottic blades, right and left hypopharynx blades, glottis blade and a post cricoids blade.

Figure 15:
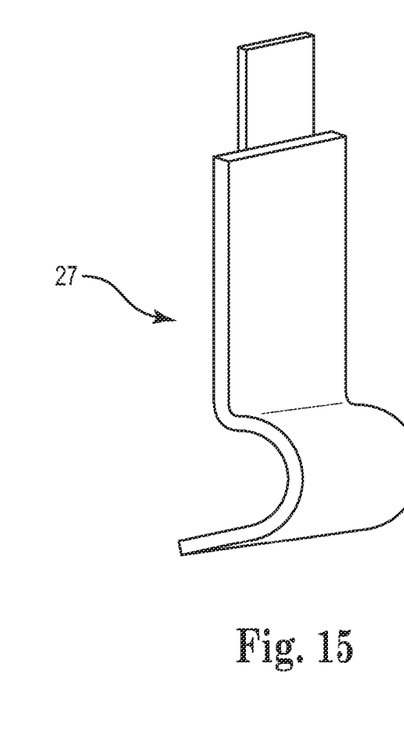
FIG. 15 is an isometric side view of a spatula blade in accordance with another embodiment of the invention.

A spatula blade 23 in accordance with another embodiment of the invention, for example, is illustrated in FIGS. 11-14. The major surface on the portion of the spatula blade 23 extending from the tip or distal end toward the proximal end is generally flat. Other than this difference, spatula blade 23 can be similar to or substantially the same as spatula blade 22 described above. FIG. 15 is an illustration of yet another alternative blade 27 having a generally hooked-shaped distal end for engaging a patients teeth and jaw.

Figure 1:
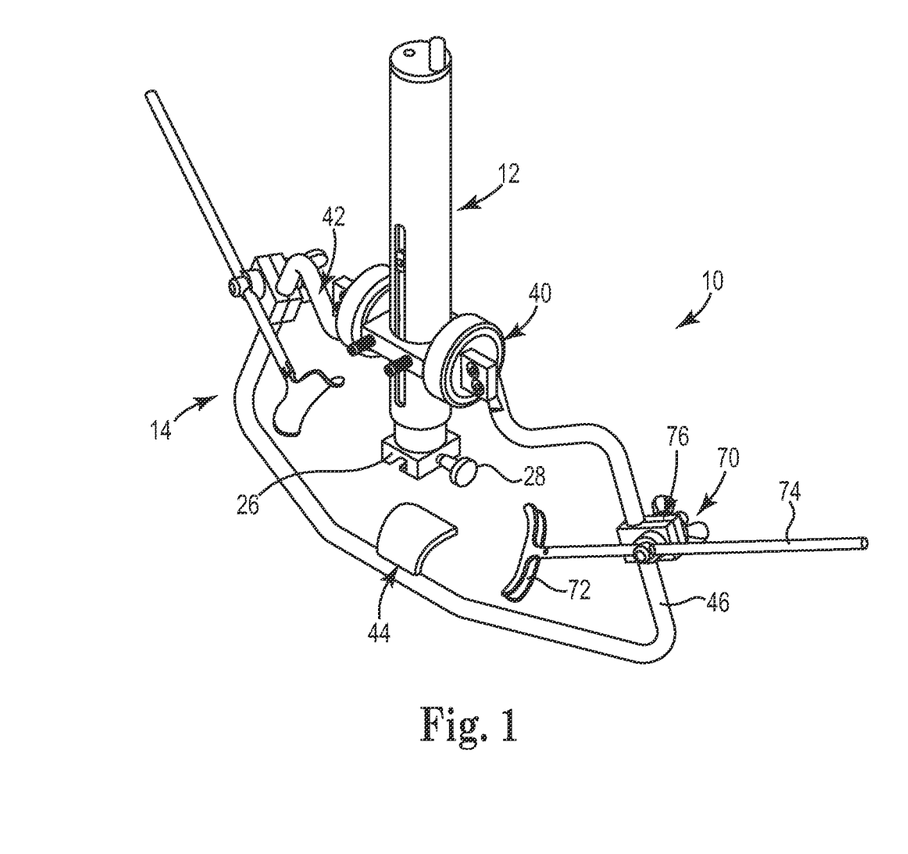
FIG. 1 is an isometric view of a transoral retractor in accordance with one embodiment of the invention.
Figure 2:
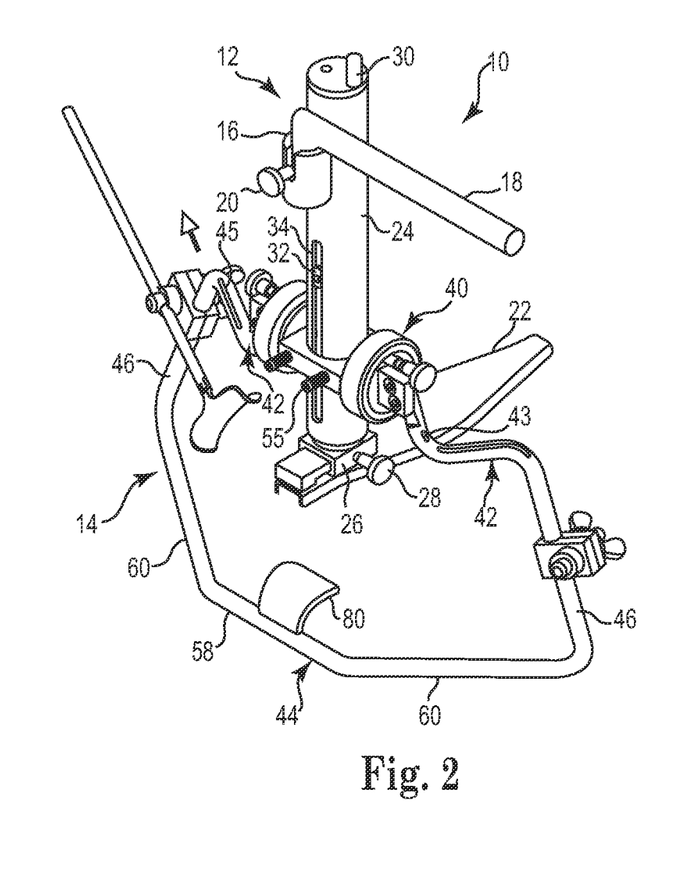
FIG. 2 is an isometric view of the transoral retractor shown in FIG. 1, shown from a different viewpoint, mounted to the arm of a support and with a spatula blade mounted to the retractor.
Figure 3:
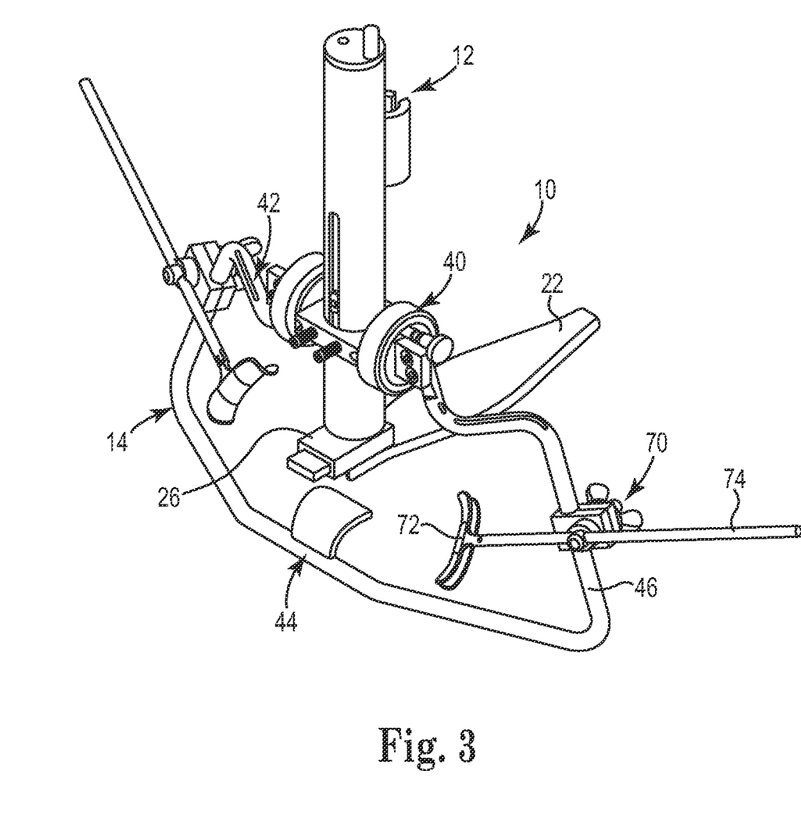
FIG. 3 is an isometric view of the transoral retractor and spatula blade shown in FIG. 1, shown from a different viewpoint.
Figure 4:
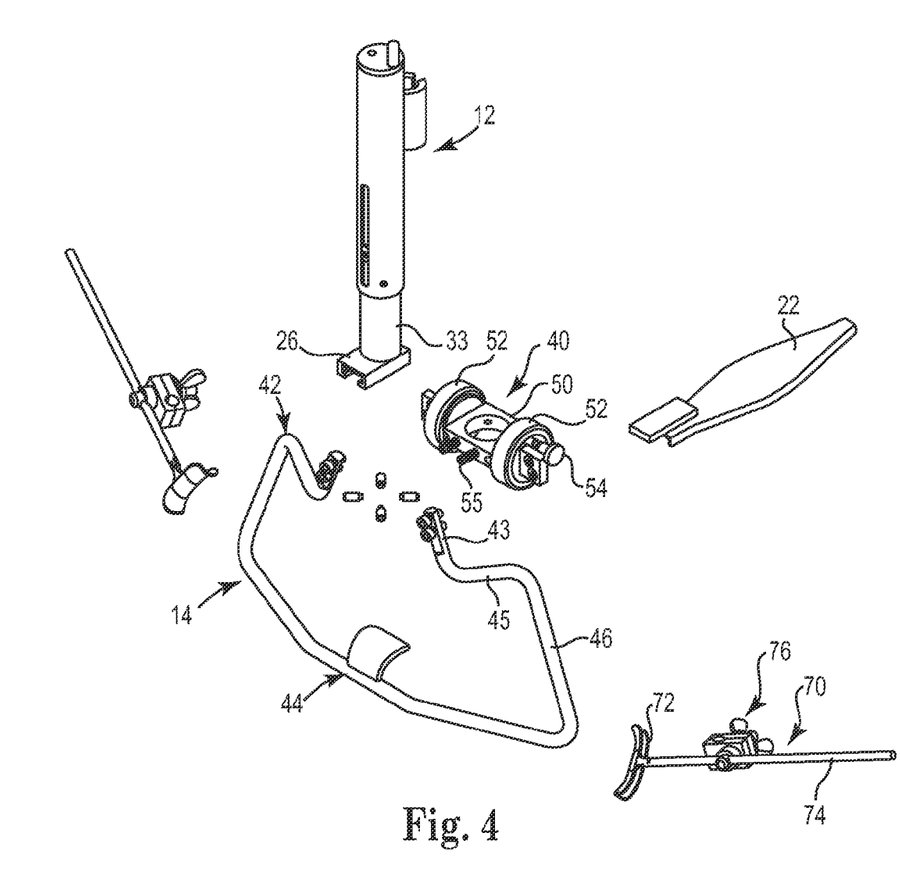
FIG. 4 is an exploded view of the transoral retractor and spatula blade shown in FIG. 1.

In operation, the retractor frame 14 serves a number of purposes. For example, it provides wide oral opening by telescoping from the handle 12 and distracting the upper and lower jaw. It also provides a fixation point for suture retraction, lateral oral commisure guards, lip protection, endotracheal tube retraction and control, and adjustable malleable retractors. Malleable retractors allow a high degree of flexibility in custom retraction to account for differing anatomy. The frame 14 is capable of pivoting, allowing the frame to be engaged on the maxillary teeth with the retractor blades inserted at any length and angle relative to the patient. The frame 14 can be locked in a neutral upward position for device insertion allowing the surgeon to position the blades optimally in the upper aerodigestive tract and then can swing down to articulate with the teeth at an optimal angle relative to the maxillary teeth. The pivoting handle 12 allows the device to interface with a variety of suspension devices and can limit neck extension possibly reducing cervical spine injury.

The invention offers a number of important advantages, especially when used in connection with surgical robots to operate on the upper aerodigestive tract. Robotics provides the surgeon with improved visualization, tremor reduction, and manual dexterity. Additionally, it facilitates operations in narrow spaces such as the aerodigestive tract which may otherwise require invasive open procedures. The invention can increase the number of patients eligible for robotic surgery, improve the safety profile of the technique, and also expand the scope of robotics in the head and neck surgery.

The invention enhances the advantage of the surgical robot for upper aerodigestive tract surgery. It enables the oral cavity to be widely opened, the oral commisures and lips to be protected and retracted, and the tongue to be retracted in a controlled manner. The surgeon is thereby provided with a clear view of the surgical field. Depending on the site of interest and the optimal vectors of retraction, the device can be used with either a gallows suspension or a standard laryngoscope chest brace. The curved retractor blades limit the pressure needed to retract the tongue and expose the distal laryngopharynx. The pivoting frame will allow the retractor blade to be inserted by the surgeon to the exact optimal depth, and then the pivoting frame can swing down, interfacing with the maxillary teeth at any angle relative to the blade.

The retractor blades protect and retract the entire body of tongue. The device allows the entire oral commisure and upper and lower lateral lip to be retracted, guarded and depressed inferiorly, providing the maximal protection and size of the oral aperture. Existing curved blades often rely upon line of sight view and do not go beyond 1 cm vertical rise with respect to the proximal end.

Although the present invention has been described with reference to preferred embodiments, those skilled in the art will recognize that changes can be made in form and detail without departing from the spirit and scope of the invention.

The invention claimed is:

1. A transoral retractor, including:
   a handle;
   a retractor blade mount;
   a telescoping extension adjustment mechanism attaching the retractor blade mount to the handle;
   a frame having proximal members, a distal transverse member including a central portion and a pair of end portions, and side members extending between the proximal members and the end portions, the frame configured with the end portions extending at an angle in a direction toward a patient from the central portion to locate the side members at transverse locations beyond a side of the patient's head and below a plane of the patient's oral commisaries; and
   a pivot mechanism for pivotally mounting the proximal members of the frame to the handle; and
   a spatula blade mounted to the retractor blade mount, wherein the spatula blade has distal and proximal ends, a long axis between the distal and proximal ends, and a major surface, wherein the major surface is curved in a direction perpendicular to the long axis to cause the distal end to be spaced by a distance of 1-4 cm with respect to the proximal end, a width profile of the spatula blade varies, and a midbody width of the blade is wider than a width of the blade at the distal and proximal ends.

2. The retractor of claim 1 wherein a proximal retractor blade surface width is optimally suited to allow the retractor to distribute force evenly along the tongue and to fit between the interdental arch of the mandible.

3. The retractor of claim 2 wherein a midbody retractor blade surface width is optimally suited to prevent the tongue from prolapsing into the oral cavity.

4. The retractor of claim 3 wherein distally, the blade width and shape is customized to the target tissue including one or more of the tonsil, base of tongue, supraglottis, glottis.

5. The retractor of claim 1 wherein the retractor blade includes side flanges.

6. The retractor of claim 1 wherein the retractor blade includes a suction port.

7. The retractor of claim 1 wherein the retractor blade is curved in first and second directions along the long axis.

* * * * *